United States Patent
Schiff et al.

(10) Patent No.: US 8,926,644 B2
(45) Date of Patent: Jan. 6, 2015

(54) LANCING DEVICE HAVING SADDLE-SHAPED TIP

(75) Inventors: David Schiff, Highland Park, NJ (US); Akilesh Sridharan, Los Angeles, CA (US); Jonathan D. Albert, Philadelphia, PA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 191 days.

(21) Appl. No.: 13/261,153

(22) PCT Filed: Jul. 30, 2010

(86) PCT No.: PCT/US2010/002139
§ 371 (c)(1),
(2), (4) Date: May 25, 2012

(87) PCT Pub. No.: WO2011/014260
PCT Pub. Date: Feb. 3, 2011

(65) Prior Publication Data
US 2012/0226123 A1 Sep. 6, 2012

Related U.S. Application Data (60) Provisional application No. 61/213,936, filed on Jul. 30, 2009.

(51) Int. Cl.
| A61B 17/14 | (2006.01) |
| A61B 5/15 | (2006.01) |
| A61B 5/151 | (2006.01) |
| A61B 5/157 | (2006.01) |

(52) U.S. Cl.
CPC ......... *A61B 5/1411* (2013.01); *A61B 5/150022* (2013.01); *A61B 5/150259* (2013.01);
(Continued)

(58) Field of Classification Search
CPC ............. A61B 5/1411; A61B 5/14532; A61B 5/15186; A61B 5/15146; A61B 5/15142; A61B 17/32093; A61B 5/151
USPC ........... 606/181, 182, 183; 600/583; 604/136, 604/137, 138, 139
See application file for complete search history.

(56) References Cited

U.S. PATENT DOCUMENTS

| 4,375,815 A | 3/1983 | Burns |
| 4,388,925 A | 6/1983 | Burns |

(Continued)

FOREIGN PATENT DOCUMENTS

| CN | 101102720 A | 1/2008 |
| EP | 1 586 270 | 10/2005 |

(Continued)

OTHER PUBLICATIONS

European Search Report issued in Application No. 10804829.9-1526 dated Nov. 16, 2012.
(Continued)

*Primary Examiner* — Jonathan W Miles
(74) *Attorney, Agent, or Firm* — Roylance, Abrams, Berdo & Goodman, L.L.P.

(57) ABSTRACT

A tip (41) for use with a lancing device (11). A wall extends upwardly from a base and forms a substantially saddle-shaped distal surface for interfacing with a patient's skin. An opening (43) extends entirely through the tip. The tip (41) is movably received by a pressure sleeve assembly. The pressure sleeve assembly includes a housing (37) and a pressure sleeve movable between first and second positions. A spring (35) is connected between the housing (37) and the pressure sleeve. A lancet (21) is rigidly fixed to the housing (37) and is covered when the pressure sleeve is in the first position and exposed through the substantially saddle-shaped distal surface (42) of the tip (41) when the pressure sleeve is in the second position. The substantially saddleshaped distal surface (42) gathers the patient's skin toward the center of the tip to facilitate expressing blood from a lanced site.

18 Claims, 13 Drawing Sheets

(52) U.S. Cl.
CPC ......... *A61B 5/150183* (2013.01); *A61B 5/1519* (2013.01); *A61B 5/157* (2013.01); *A61B 5/15113* (2013.01); *A61B 5/150503* (2013.01); *A61B 5/150633* (2013.01); *A61B 5/15142* (2013.01); *A61B 5/150068* (2013.01); *A61B 5/15105* (2013.01); *A61B 5/150412* (2013.01)
USPC ...................................................... 606/181

(56) References Cited

U.S. PATENT DOCUMENTS

| | | | | |
|---|---|---|---|---|
| 4,416,279 | A | | 11/1983 | Lindner |
| 4,442,836 | A | * | 4/1984 | Meinecke et al. ............ 606/182 |
| 4,449,529 | A | | 5/1984 | Burns |
| 4,527,561 | A | | 7/1985 | Burns |
| 4,535,769 | A | | 8/1985 | Burns |
| 4,539,988 | A | * | 9/1985 | Shirley et al. ................. 606/182 |
| 4,553,541 | A | | 11/1985 | Burns |
| 4,577,630 | A | | 3/1986 | Nitzsche |
| 4,889,117 | A | * | 12/1989 | Stevens .......................... 606/181 |
| 5,014,718 | A | | 5/1991 | Mitchen |
| 5,070,886 | A | | 12/1991 | Mitchen |
| 5,324,302 | A | | 6/1994 | Crouse |
| 5,624,458 | A | | 4/1997 | Lipscher |
| 5,709,699 | A | | 1/1998 | Warner |
| 5,857,983 | A | | 1/1999 | Douglas |
| 5,951,493 | A | * | 9/1999 | Douglas et al. ............... 600/583 |
| 6,071,250 | A | | 6/2000 | Douglas |
| 6,322,574 | B1 | | 11/2001 | Lloyd |
| 6,558,402 | B1 | | 5/2003 | Chelak |
| 6,589,260 | B1 | | 7/2003 | Schmelzeisen-Redeker |
| 6,706,049 | B2 | * | 3/2004 | Moerman ..................... 606/181 |
| 6,752,817 | B2 | | 6/2004 | Flora |
| 6,793,633 | B2 | | 9/2004 | Douglas |
| 7,192,405 | B2 | | 3/2007 | DeNuzzio |
| 7,291,159 | B2 | | 11/2007 | Schmelzeisen-Redeker |
| 7,678,126 | B2 | * | 3/2010 | Schraga ........................ 606/181 |
| 7,811,302 | B2 | * | 10/2010 | Steg .............................. 606/181 |
| 2002/0087180 | A1 | | 7/2002 | Searle |
| 2002/0169393 | A1 | | 11/2002 | Cunningham |
| 2004/0204662 | A1 | | 10/2004 | Perez et al. |
| 2005/0215923 | A1 | * | 9/2005 | Wiegel ........................... 600/573 |
| 2005/0234489 | A1 | | 10/2005 | Allen |
| 2005/0234491 | A1 | * | 10/2005 | Allen et al. ................... 606/181 |
| 2008/0195131 | A1 | * | 8/2008 | Flynn et al. ................... 606/181 |
| 2009/0105613 | A1 | * | 4/2009 | Nishiuchi ...................... 600/583 |

FOREIGN PATENT DOCUMENTS

| | | |
|---|---|---|
| JP | 61-77003 | 5/1986 |
| JP | 2005-305158 | 11/2005 |
| JP | 2009-136302 | 6/2009 |
| WO | 97/08986 | 3/1997 |
| WO | 2005/096943 | 10/2005 |
| WO | 2006/058654 | 6/2006 |

OTHER PUBLICATIONS

Chinese Office Action issued in Application No. 201080041510.3 dated Sep. 24, 2013.
Chinese Office Action issued in CN Application No. 201080041510.3 dated Jan. 30, 2014, and English translation thereof.
Official Notice of Rejection, dated Aug. 5, 2014, in related Japanese Patent Application No. 2012-522815, and English translation thereof.

* cited by examiner

| SADDLE NAME | MAX OD (in) | MIN OD (in) | MAX ID (in) | MIN ID (in) | ANGLE YZ PLANE (deg) | ANGLE XZ PLANE (deg) | ACTIVE SURFACE AREA (in^2) | DEPTH SETTING (in) |
|---|---|---|---|---|---|---|---|---|
| saddle_circle_01 | 0.45 | 0.4 | 0.2 | 0.2 | 45 | -15 | 0.1 | 0.42 |
| saddle_steep_circle_01 | 0.45 | 0.4 | 0.2 | 0.2 | 60 | -20 | 0.11 | 0.42 |
| | | | | | | | | 0.42 |
| saddle_oval_01 | 0.52 | 0.35 | 0.4 | 0.2 | 45 | -15 | 0.103 | 0.42 |
| saddle_steep_oval_01 | 0.52 | 0.35 | 0.4 | 0.2 | 60 | -20 | 0.11 | 0.42 |

ANGULAR RELATIONSHIPS
IN DEGREES

| | CENTER LINE |
|---|---|
| L1 | 27.403 |
| L2 | 68.166 |
| L3 | 17.66 |
| L4 | 72.3173 |

FIG.20

ANGULAR RELATIONSHIPS
IN DEGREES

| | CENTER LINE |
|---|---|
| L5 | 17.257 |
| L6 | 23.497 |

FIG.21

NO DOWNWARD PRESSURE
APPLIED

FIG.22

DOWNWARD PRESSURE ENABLES/
TRIGGERS LANCING

AVERAGE BLOOD VOLUME GENERATION (μL)

| OVAL | CIRCLE | STEEP OVAL | STEEP CIRCLE |
|---|---|---|---|
| 0.31875 | 0.1325 | 0.2625 | 0.16875 |

LANCING DEVICE HAVING SADDLE-SHAPED TIP

CROSS REFERENCE TO RELATED APPLICATION

This application claims the benefit under 35 U.S.C. §119(a) and §119(e) of U.S. Provisional Patent Application Ser. No. 61/213,936, filed Jul. 30, 2009, the entire content of which is hereby incorporated by reference.

FIELD OF THE INVENTION

The present invention relates to a lancing device that does not require the user to "milk" blood from a lanced site. More particularly, the present invention relates generally to a lancing device having a saddle-shaped tip to express blood from an incision. Still more particularly, the present invention generally relates to a saddle-shaped tip for a lancing device that gathers flesh toward the center of the tip to facilitate expressing blood from a lanced site.

BACKGROUND OF THE INVENTION

Self-monitoring of blood glucose levels requires a user to extract a discrete volume of capillary blood (typically from the fingertip) and place the extracted blood on a disposable element for analysis. The blood extraction is generally accomplished by lancing and subsequently "milking" the lanced site to express a sufficient volume of blood for analysis. After the user has produced a skin opening in a finger by lancing, the finger is "milked", i.e., massaged or squeezed, to draw blood through the opening.

While blood volume requirements of electromechanical sensors have dropped to sub-microliter levels, users typically still need to "milk" the lanced sites to express enough blood to trigger a sensor. The "milking" process adds another step and level of complexity to the task of obtaining a blood glucose measurement.

Figure 1:
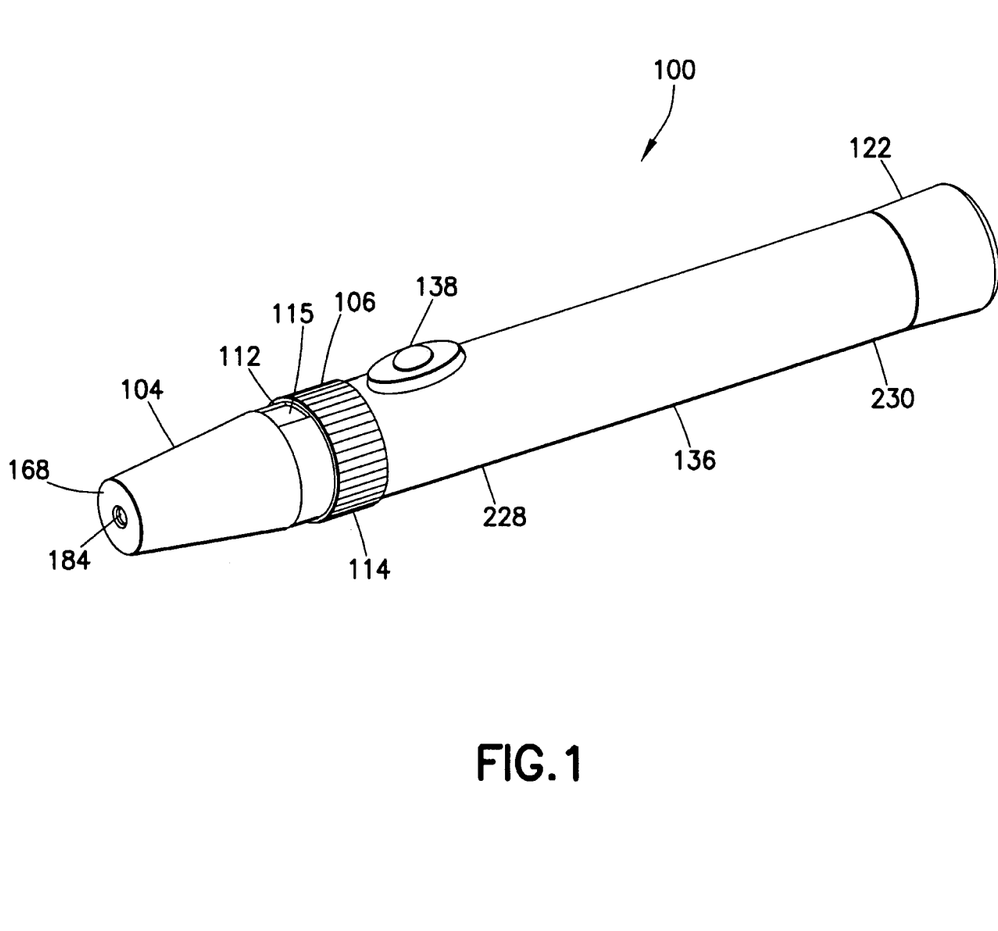
FIG. 1 is a perspective view of a lancing device.

A typical lancing device 100 is shown FIG. 1. A nose portion 104 has a surface 168 at a distal end for pressing against a patient's flesh. A lancet stylet passes through a nose orifice 184 formed in the nose portion 104 when activated by the release member 138. Indication marks of the position of the lancet stylet are visible through a window 112, which is covered by a translucent lens 115. According to one embodiment, however, the translucent lens 115 is omitted. An adjustment collar 106 is rotatable around the nose portion 104 to set the desired depth of penetration. Bumps or knurls 114 on the adjustment collar 106 facilitate rotation of the adjustment collar. A distal end 228 of a body assembly 136 is connected to the nose portion 104. A knob cap 122 is disposed at a proximal end 230 of the body assembly 136. The assembly and operation of the lancing device 100, as shown in FIG. 1, is described in commonly-owned U.S. Pat. No. 6,558,402, which issued on May 6, 2003, and is hereby incorporated by reference in its entirety.

Devices currently exist that attempt to eliminate the need to "milk" a lanced site. For example, one device, Bayer's Vaculance®, applies a vacuum after lancing to cause the skin to bulge upwardly to better express blood. Another device, Abbott's Soft-Tact™, applies a vacuum both before and after lancing to stretch the skin to better express blood. However, these vacuum devices are intended for off-finger use exclusively. Accordingly, a need exists for a lancing device that does not require the user to "milk" the lanced site to express blood and is usable on the user's fingertip.

Furthermore, vacuum application requires sufficient surface area to create a seal between the vacuum device and the user's skin. Creating a vacuum on a topographically non-uniform surface, such as a fingertip, is difficult. Typically, the user uses a flat surface as a support to successfully achieve the necessary seal. Accordingly, a need exists for a lancing device that does not require a seal around the lanced site or a flat surface to support the lancing device.

SUMMARY OF THE INVENTION

In accordance with an aspect of the present invention, a lancing device produces a sufficient volume of blood quickly without unnecessary manual or device-dependent manipulation.

In accordance with another aspect of the present invention, a lancing device expresses blood without requiring the user to remove the lancing device and manually "milk" the lanced site.

In accordance with another aspect of the present invention, the lancing device has a saddle-shaped tip that moves flesh towards the center of a lanced site and a pressure sleeve that compresses with minimum threshold force.

A lancing device in accordance with embodiments of the present invention provides a simple device and method by which a user may quickly obtain a sufficient volume of blood without unnecessary manual or device-dependent manipulation. Downward pressure is simply applied to the tip of the lancing device, and the user is not required to remove the lancing device after lancing to manually express blood. The lancing device has a tip shaped to gather flesh toward the center of the lanced site and is coupled with a pressure sleeve that compresses with minimum threshold force.

The foregoing objects are attained by providing a tip for use with a lancing device in which the tip includes a base having an outer perimeter and a wall extending upwardly from the base and forming a substantially saddle-shaped distal surface for interfacing with a patient's skin. An opening extends entirely through the tip.

The foregoing objects are also attained by providing a lancing device including a tip having a substantially saddle-shaped distal surface for interfacing with a patient's skin and a pressure sleeve assembly movably receiving the tip. The pressure sleeve assembly includes a housing and a pressure sleeve movable between first and second positions. A spring is connected between the housing and the pressure sleeve. A lancet is rigidly fixed to the housing such that the lancet is covered when the pressure sleeve is in the first position and exposed through the substantially saddle-shaped distal surface of the tip when the pressure sleeve is in the second position.

The foregoing objects are also attained by providing a method of drawing blood. A distal surface of a tip of a lancing device interfaces with a patient's skin at a lancing site. The distal surface of the tip is substantially saddle-shaped. A needle is passed through the saddle-shaped distal surface of the tip to lance the patient's skin at the lancing site.

These and other objects, advantages, and salient features of the invention will become apparent from the following detailed description, which, taken in conjunction with the annexed drawings, discloses exemplary embodiments of the invention.

BRIEF DESCRIPTION OF THE DRAWINGS

The above benefits and other advantages of the various embodiments of the present invention will be more apparent from the following detailed description of exemplary embodiments of the present invention and from the accompanying drawing figures, in which.

Throughout the drawings, like reference numbers will be understood to refer to like parts, components and structures.

DETAILED DESCRIPTION OF THE EXEMPLARY EMBODIMENTS

The exemplary embodiments of the present invention disclosed herein provide a lancing device that eliminates the need for "milking." The geometry of the tip is designed to elicit the requisite volume of blood needed for a blood glucose measurement by simply applying downward pressure. This pressure may be applied either before or after lancing, or both. Empirical tests have been performed to determine the advantages of the aforementioned various pressure application states.

Figure 2:
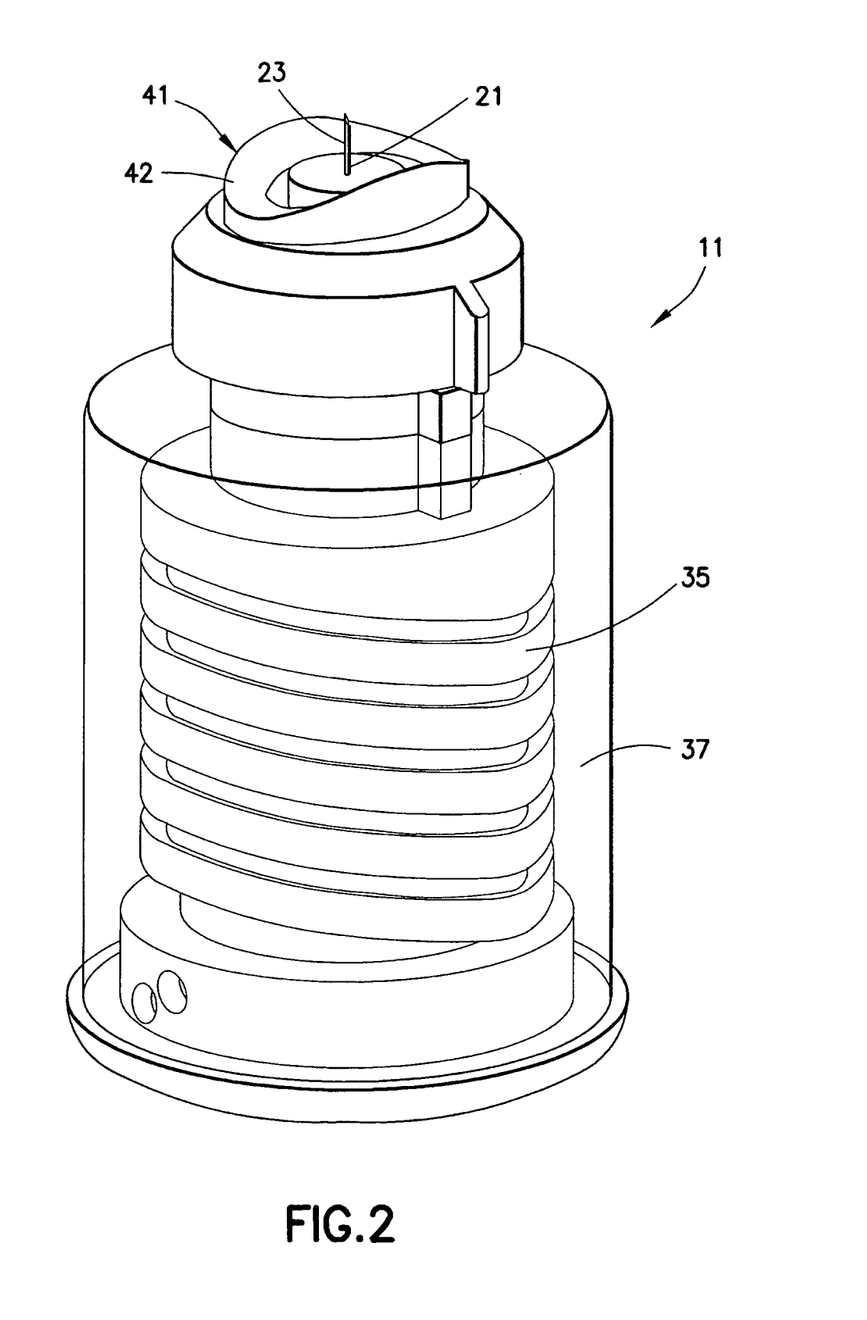
FIG. 2 is a perspective view of a lancing device according to an exemplary embodiment of the present invention in which the tip is substantially saddle-shaped.
Figure 22:
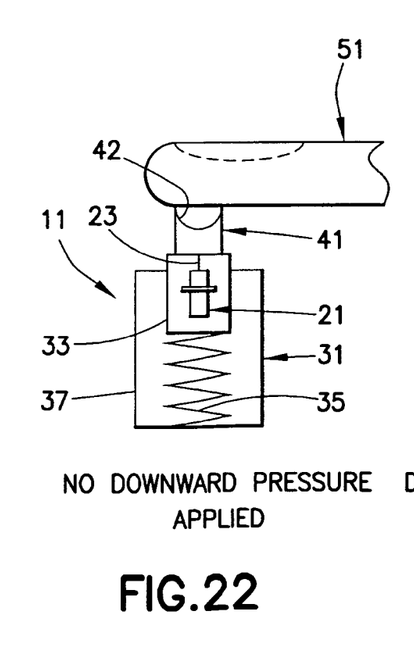
FIG. 22 is an illustration of a lancing device according to an exemplary embodiment of the present invention prior to a user applying a downward force with a fingertip.
Figure 23:
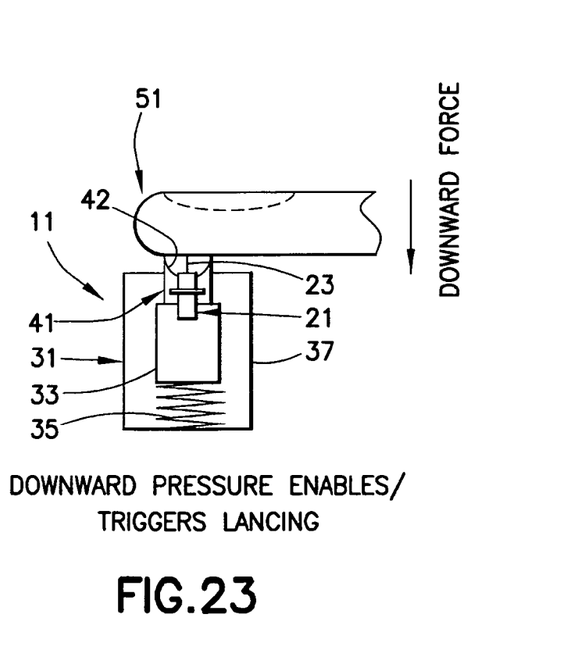
FIG. 23 is an illustration of the lancing device of FIG. 22 after the user has applied downward force with the fingertip.

As shown in FIGS. 2, 22 and 23, a lancing device 11 according to an exemplary embodiment of the present invention includes a tip 41 and a pressure sleeve assembly 31. The lancing device 11 expresses blood from a small incision by raising the capillary bed beneath the incision site. The capillary bed is raised by the two complementary devices, i.e., the tip 41 and the pressure sleeve assembly 31. The tip 41 may be clear or opaque. A clear tip allows a user to see to visibly detect the amount of blood generated and to determine whether additional pressure needs to be applied to increase the volume of blood generated.

The tip 41 contacts the skin of a finger 51 and causes the skin to bulge on the side of the fingertip surrounding the lanced site. A distal surface 42 of the tip 41 has a saddle-shape that houses a portion of the fingertip within a given diameter. The tip also has an angled interior that causes the flesh to bulge toward the center of the lanced site. Various saddle-shape geometries and angled interiors are shown in FIGS. 3-14 that gather the flesh around a lanced site, thereby facilitating expressing blood from the lanced site. Accordingly, the saddle-shaped tip according to exemplary embodiments of the present invention can also be used to lance sites other than the fingertip.

The pressure sleeve assembly 31 mates with the saddle-shaped tip 41 and includes a compression spring 35 in a housing 37. When the saddle-shaped tip 41 is located on a side of a user's finger 51, the user then pushes down on the pressure sleeve 33, thereby causing additional flesh to bulge upwardly. The compression spring 35 may be sized as desired. For example, a spring may be used that compresses completely at a force of two pounds (8.9 newtons). Accordingly, the minimum force a user must apply prior to lancing is two pounds (8.9 newtons). After lancing, the user may relieve and reapply pressure to the pressure sleeve 33 any number of times until the desired amount of blood is measured, which may be measured optically, electrically or mechanically. Requiring a user to apply a minimum force prior to lancing ensures that the skin conforms with the tip's inner angle, thereby raising the capillary bed. The pressure also causes the skin to stretch, thereby resulting in a larger wound than is created through conventional lancing, as well as facilitating expressing blood from the lanced site.

The lancet 21 may be integrally formed with the lancing device 11 such that the entire lancing device is disposable after being used. Alternatively, the lancet 21 may be removably disposed in the lancing device 11, such that after being used only the lancet 21 is removed and is replaced with a new lancet.

As shown in FIGS. 22 and 23, a saddle-shaped tip 41 is connected to a pressure sleeve 33 of a pressure sleeve assembly 31. The saddle-shaped tip 41 and the pressure sleeve 33 are slidably connected to a housing 37 of the pressure sleeve assembly 31. A compression spring 35 is disposed between the pressure sleeve 33 and an interior surface of the housing 37. A conventional lancet 21 is disposed within the pressure sleeve 33 such that when the spring 35 is not compressed, as shown in FIG. 22, a needle 23 is not exposed through the saddle-shaped tip 41. When a user's finger 51, applies sufficient downward pressure on the saddle-shaped tip 41, the saddle-shaped tip 41 and the pressure sleeve 33 move downwardly and compress the spring 35, as shown in FIG. 23. An opening, such as opening 43 of FIG. 5, extends entirely through the tip 41 to allow the lancet 21 to pass therethrough. The lancet 21, including the needle 23, is rigidly fixed such that the lancet and needle do not move when downward pressure is applied, thereby exposing the needle 23 through the saddle-shaped tip 41 to lance the user's finger 51, as shown in FIGS. 22 and 23.

Figure 3:
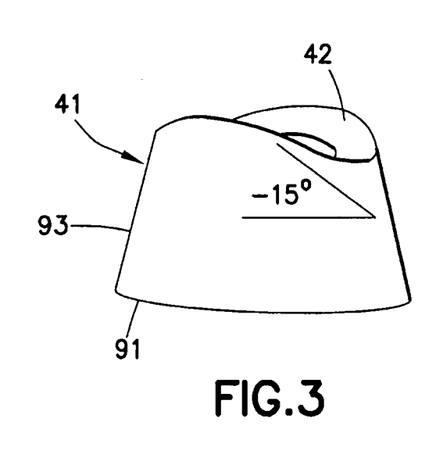
FIG. 3 is a perspective view of an saddle-shaped tip having an oval cross section for the lancing device where the minor saddle angle is approximately 15 degrees.
Figures 4, 5:
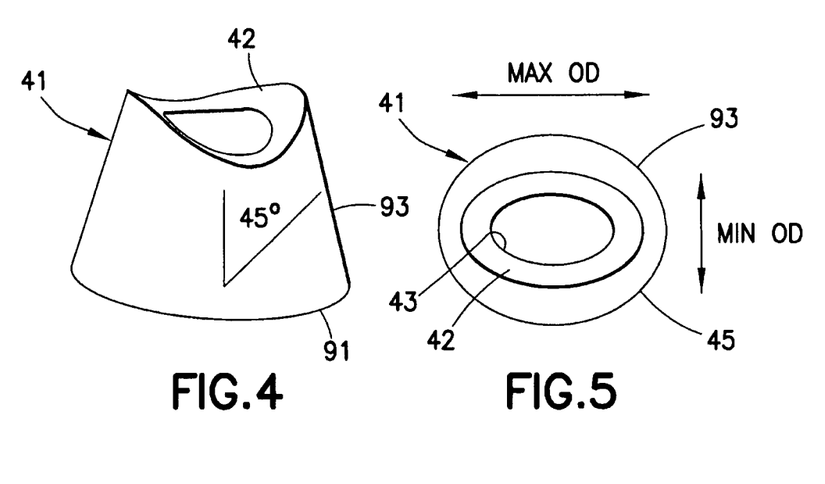
FIG. 4 is another perspective view of the tip of FIG. 3 where the major saddle angle is approximately 45 degrees.
FIG. 5 is a top plan view of the tip of FIG. 3 showing the tip opening having an oval shape.

Various geometries of the saddle-shaped tip 41 are shown in FIGS. 3-14. A first exemplary embodiment of the saddle-shaped tip is shown in FIGS. 3-5. The tip 41 has a base 91 and a wall 93 extending upwardly therefrom and forming a substantially saddle-shaped distal surface 42, which interfaces with a patient's skin. An opening 43 extends entirely through the tip 41.

Isometric views of a saddle-shaped tip are shown in FIGS. 3 and 4 and show the angle of the tip in the X-Z and Y-Z planes, respectively. As detailed in the table of FIG. 15, the angles in the X-Z (minor) and Y-Z (major) planes are approximately 15 and 45 degrees, respectively. FIG. 5 is a top plan view of the saddle-shaped tip 41 in which the tip has an oval-shaped opening 43 and an oval outer circumference 45. However, the invention is not limited to the various angles and geometries shown in the drawings and tables. The saddle-shaped tip conforms to the sides and pad of the fingertip, and the asymmetric shape of the tip conforms to the asymmetry of most fingerpads.

Figure 6:
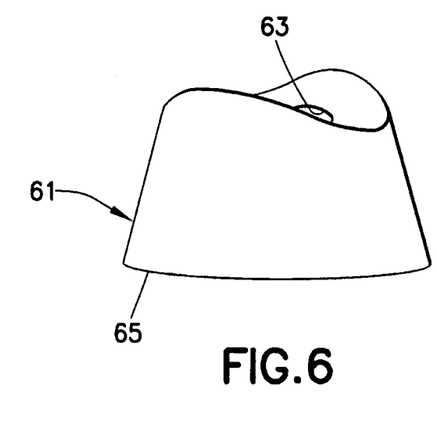
FIGS. 6 and 7 are perspective views of another exemplary embodiment of a saddle-shaped tip for the lancing device in which the tip opening is substantially circular.
Figure 7:
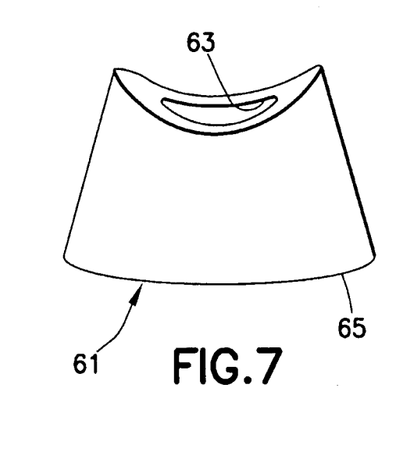
Figure 8:
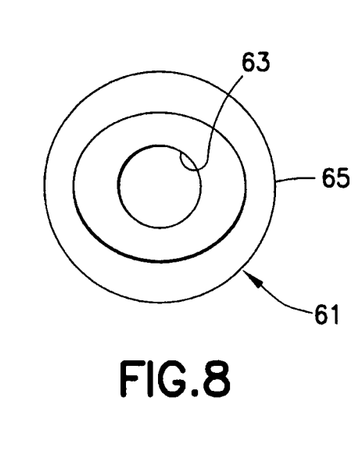
FIG. 8 is a top plan view of the tip of FIGS. 6 and 7.

A second exemplary embodiment of the saddle-shaped tip 61 is shown in FIGS. 6-8. Isometric views of a saddle-shaped tip are shown in FIGS. 6 and 7 and show the angle of the tip in the X-Z and Y-Z planes, respectively. As detailed in the table of FIG. 15, the angles in the X-Z (minor) and Y-Z (major) planes are approximately 20 and 60 degrees, respectively. FIG. 8 is a top plan view of the saddle-shaped tip 61 in which the tip has a substantially circular opening 63 and a substantially circular outer circumference 65.

Figure 9:
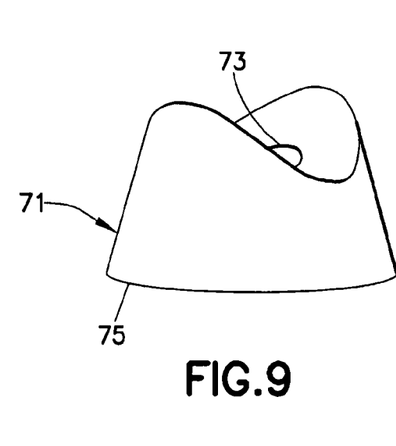
FIGS. 9 and 10 are perspective views of another exemplary embodiment of a saddle-shaped tip for the lancing device showing a steep circular tip.
Figure 10:
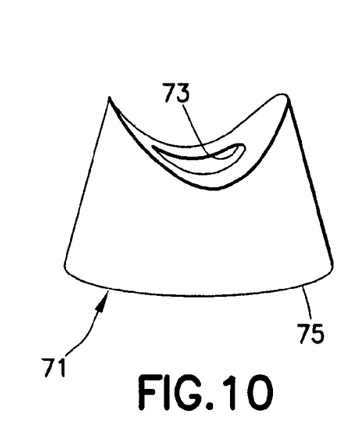
Figure 11:
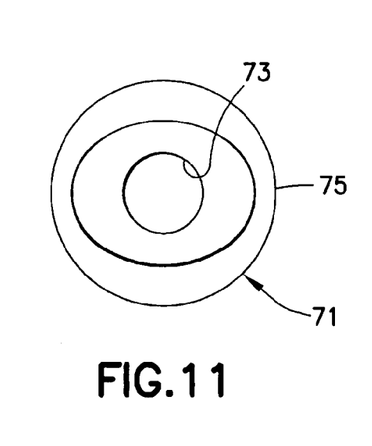
FIG. 11 is a top plan view of the tip of FIGS. 9 and 10.

A third exemplary embodiment of the saddle-shaped tip 71 is shown in FIGS. 9-11. Isometric views of a saddle-shaped tip are shown in FIGS. 9 and 10 and show the angle of the tip in the X-Z and Y-Z planes, respectively. As detailed in the table of FIG. 15, the angles in the X-Z (minor) and Y-Z (major) planes are approximately 15 and 45 degrees, respectively. FIG. 11 is a top plan view of the saddle-shaped tip 71 in which the tip has a substantially circular opening 73 and a substantially circular outer circumference 75.

Figure 12:
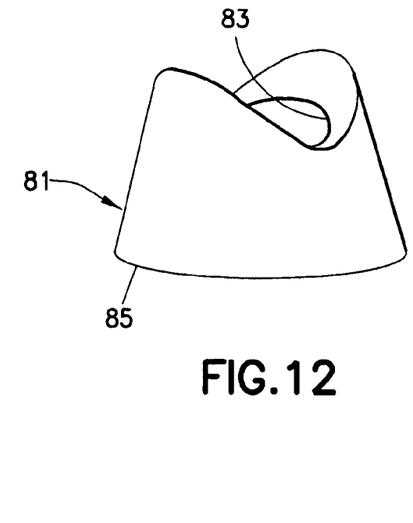
FIGS. 12 and 13 are perspective views of another exemplary embodiment of a saddle-shaped tip for the lancing device showing a steep oval tip.
Figure 13:
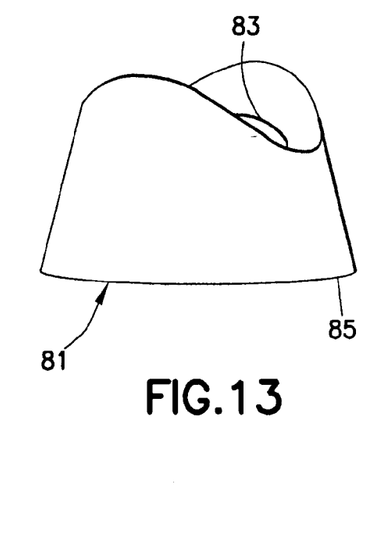
Figure 14:
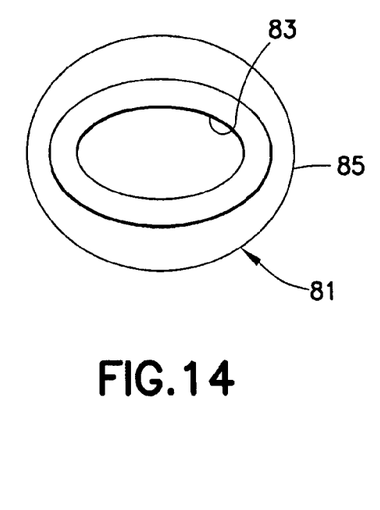
FIG. 14 is a top plan view of the tip of FIGS. 12 and 13.

A fourth exemplary embodiment of the saddle-shaped tip 81 is shown in FIGS. 12-14. Isometric views of a saddle-shaped tip are shown in FIGS. 12 and 13 and show the angle of the tip in the X-Z and Y-Z planes, respectively. As detailed in the table of FIG. 15, the angles in the X-Z (minor) and Y-Z (major) planes are approximately 20 and 60 degrees, respectively. FIG. 14 is a top plan view of the saddle-shaped tip 81 in which the tip has an oval-shaped opening 83 and an oval outer circumference 85.

A polygonal hand model having 240 individual surfaces was used to create a model of a human fingertip having a maximum length of approximately one inch, a width of approximately 0.5 inches (1.27 cm) and a depth of approximately 0.4 inches (1.016 cm). The model was used to create a mesh projected on the various surfaces of the finger and located around the region used in empirical testing of various saddle-shaped tips. In FIG. 16, the length of the meshed region is approximately 0.5 inches (1.27 cm), which is approximately equal to the value of the maximum outer diameter of the four tips listed in the table of FIG. 15.

Figure 17:
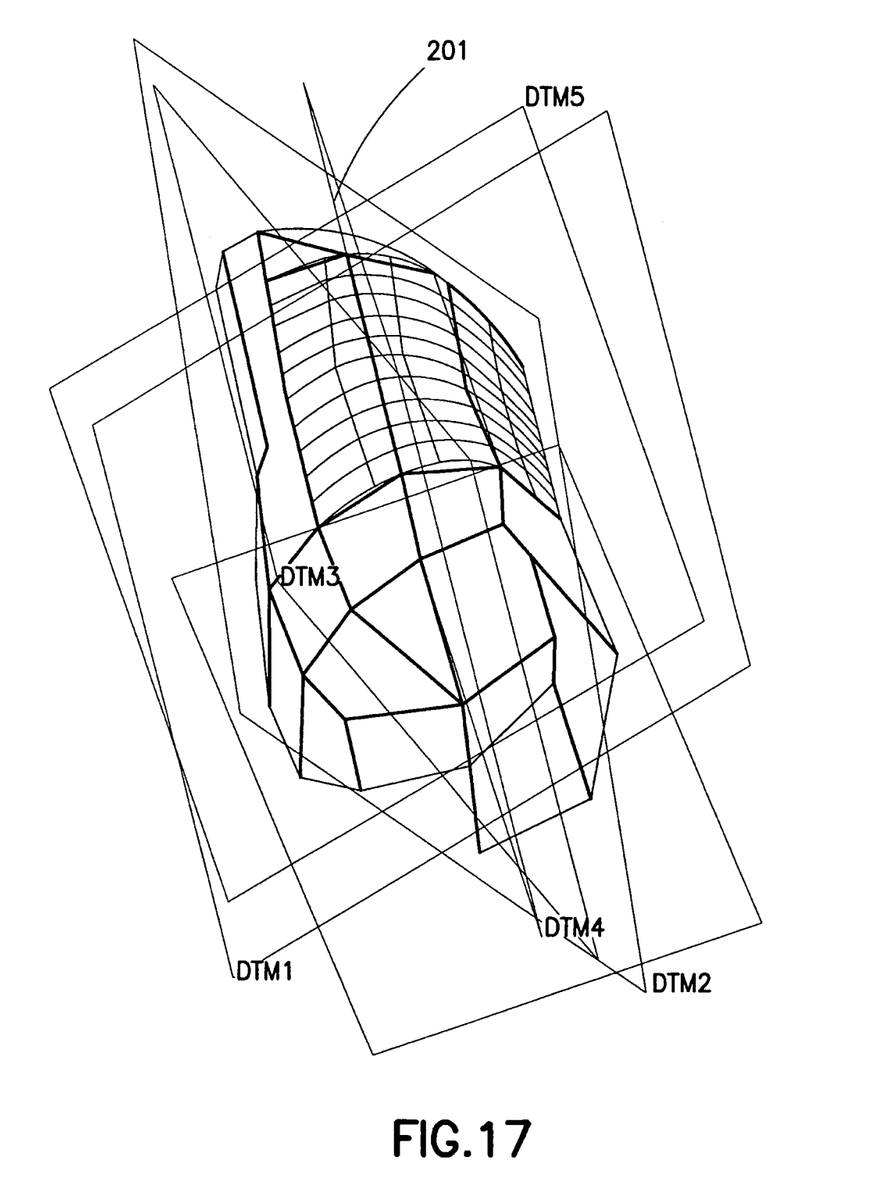
FIG. 17 illustrates various planes on the mesh used to calculate angles across the side of the fingertip in the x-direction and the angles between these planes correspond to the major saddle angles.

The mesh was used to evaluate the angular variations in finger topology in the X-Z and Y-Z planes. As shown in FIG. 17, planes are created along the center and edges of the mesh to measure the angles between them. The fingertip mesh was generated from the ring finger of a right hand, and thus, is on the "off-side" with respect to where most right-handed diabetics typically lance themselves.

Figure 18:
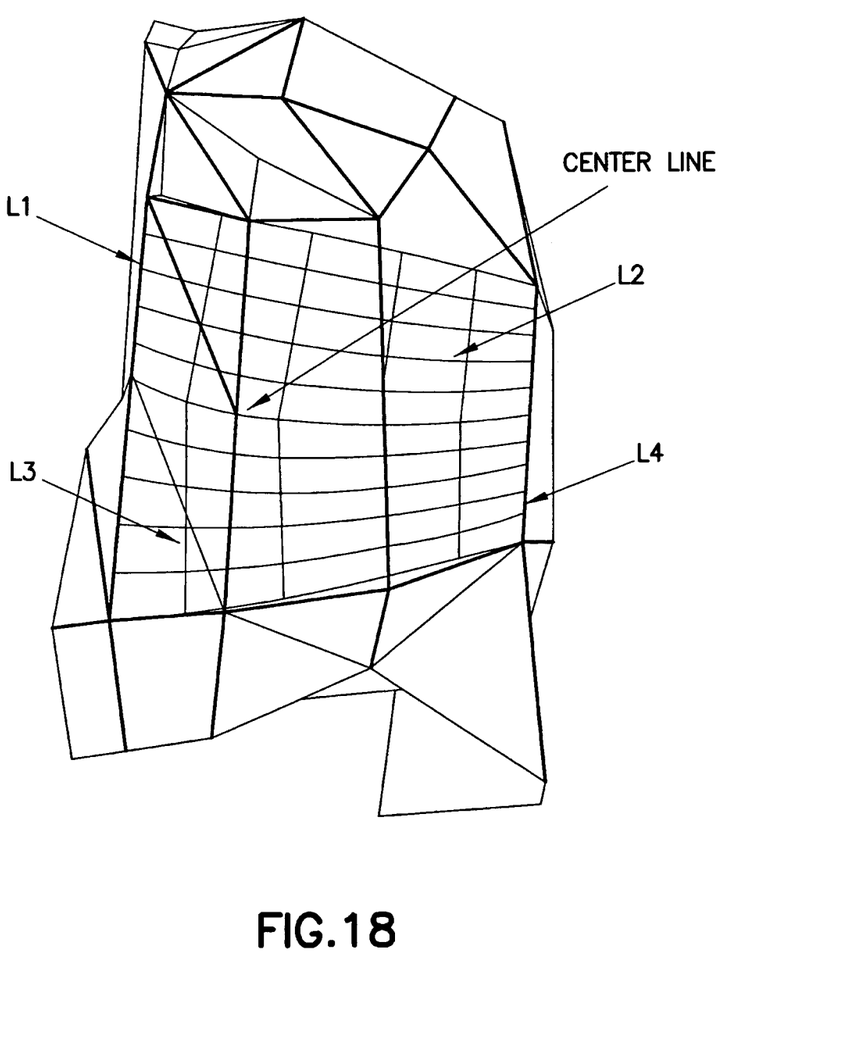
FIG. 18 shows the lines on the mesh used to create the planes visible in FIG. 16.
Figure 19:
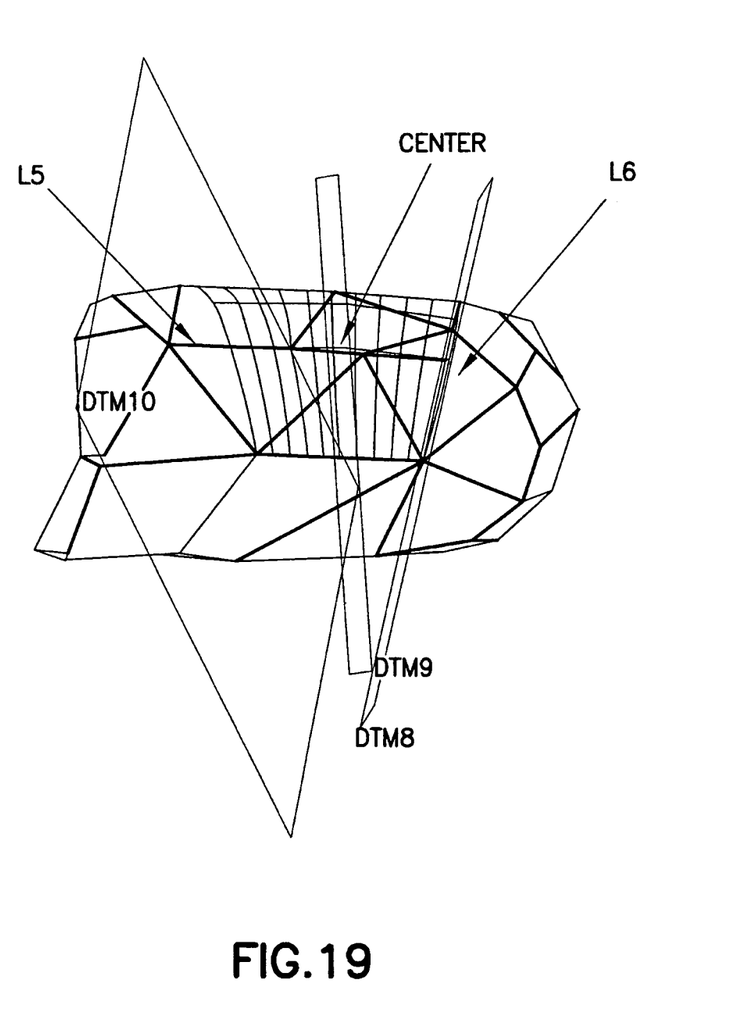
FIG. 19 shows the lines and planes used to calculate angles across the side of the fingertip in the Y-direction and the angles between these planes correspond to the minor saddle angles.
Figure 20:
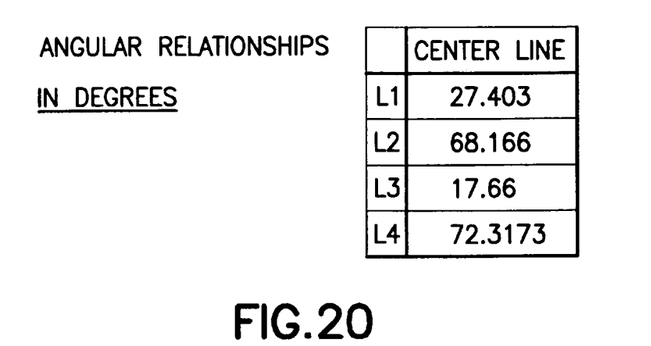
FIGS. 20 and 21 are tables of the angles in the X-Z and Y-Z planes, respectively, with respect to the lines shown in FIGS. 18 and 19.
Figure 21:
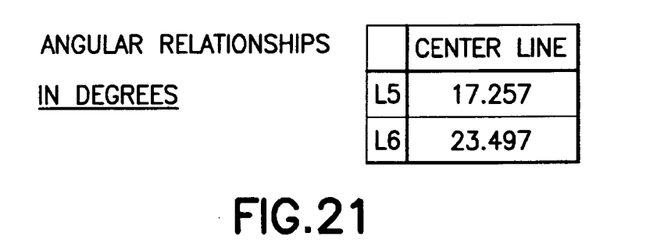

The plane 201 of FIG. 17 passes through the "top-most" points on the fingertip and is the center. The vertical lines of FIG. 18 are labeled to define planes subsequently used to define angles in the X-Z plane. These measurements are summarized in the table of FIG. 20. The horizontal lines of FIG. 19 are labeled to define planes subsequently used to define angles in the Y-Z plane. These measurements are summarized in the table of FIG. 21. The data presented in the tables of FIGS. 20 and 21 is an average of over 120 angular relationships taken over the length and width of the mesh.

Figure 15:
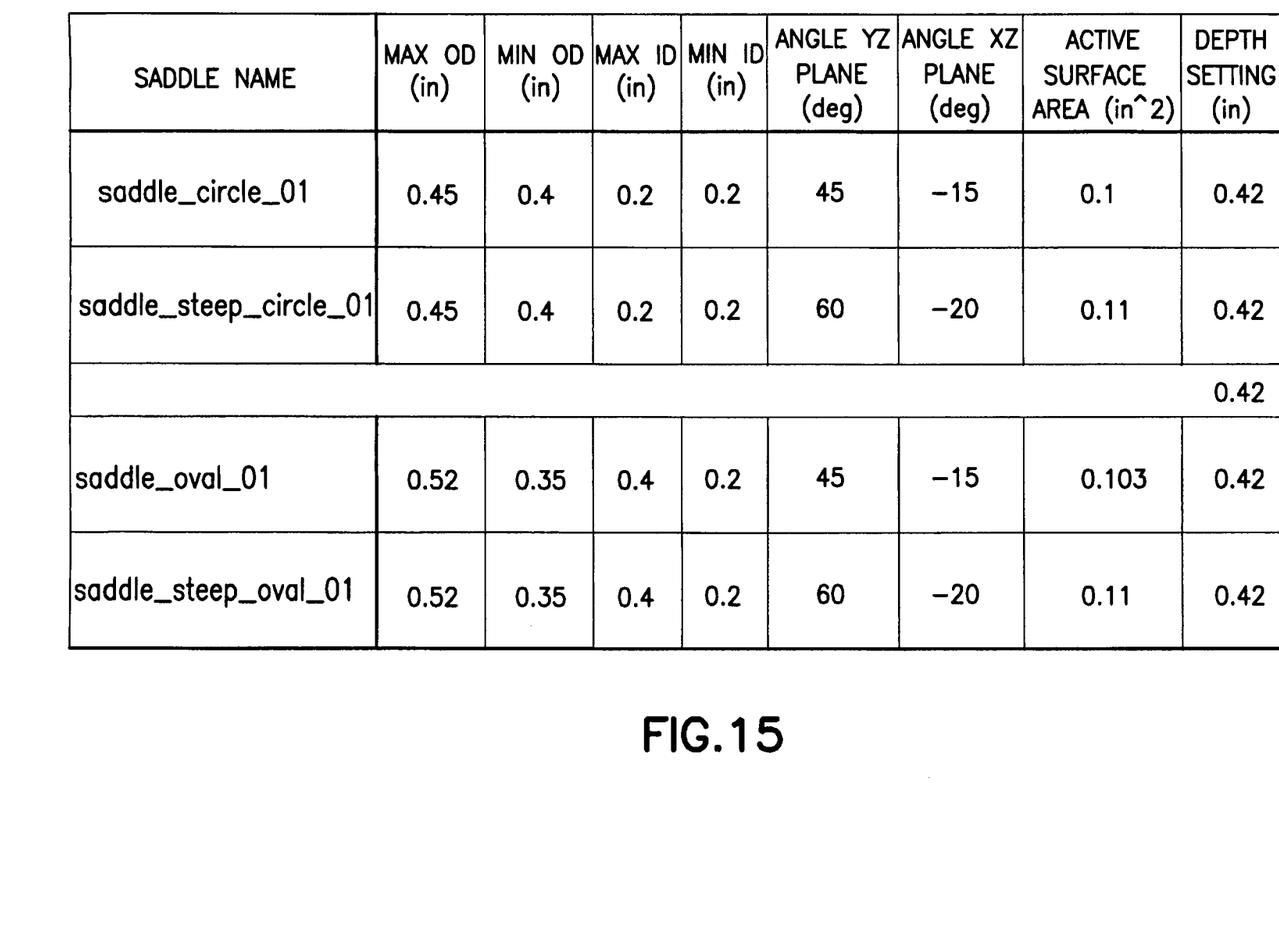
FIG. 15 is a table of the various dimensions associated with the exemplary saddle designs shown in FIGS. 3-14.
Figure 16:
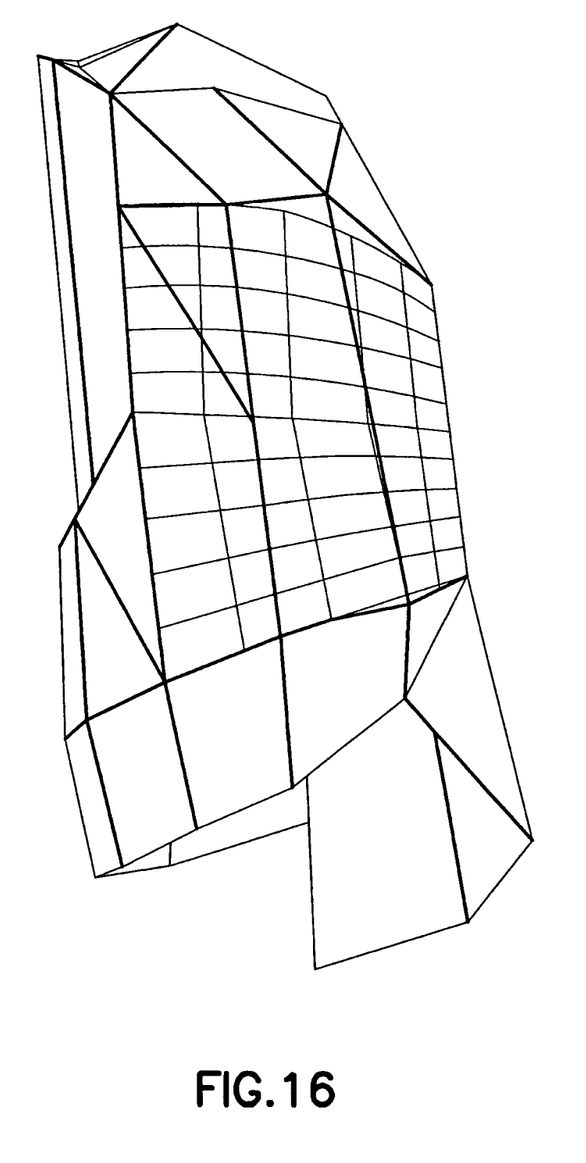
FIG. 16 is a finger model having a topographic mesh created on the side of the finger in which the mesh corresponds to the saddle-shaped tips of FIGS. 2-14.

These results show that the averages of these measurements fall within the range specified in the table of FIG. 15, i.e., that the angle in the Y-Z (major) plane is between approximately 45 and 60 degrees and that the angle in the X-Z (minor) plane is between approximately 15 and 20 degrees. The results also show the asymmetry of the human fingertip. The tip may also be designed to be asymmetric to conform to the human fingertip and to apply force non-uniformly.

Figure 24:
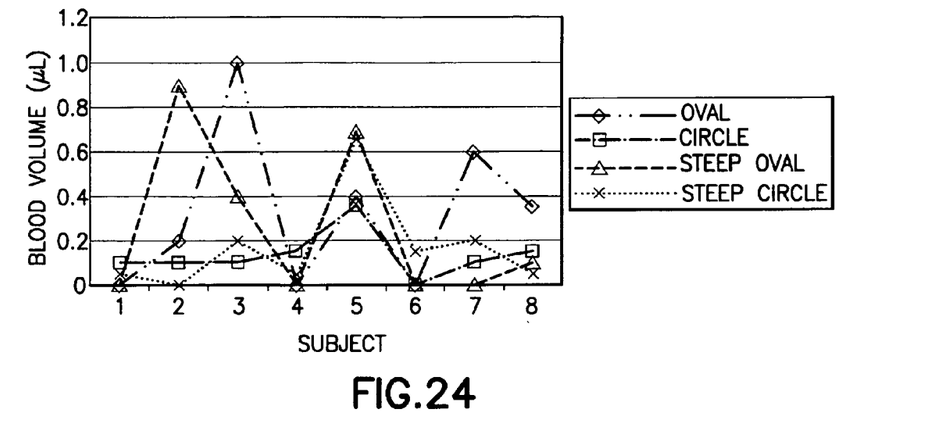
FIG. 24 is a chart showing the effectiveness of using tip geometries specified in FIG. 15 with respect to blood volume generation.
Figure 25:
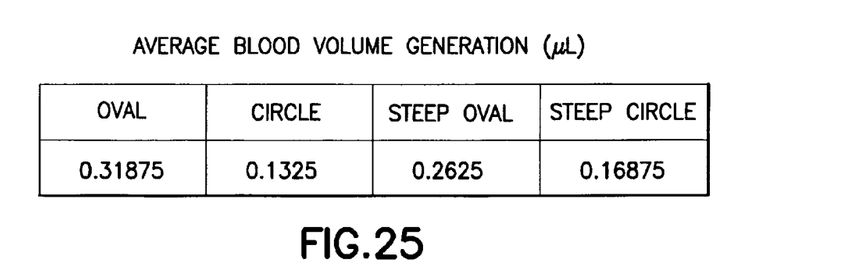
FIG. 25 is a table of the generated blood volume for the exemplary saddle-shaped tips of FIGS. 3-14.

FIG. 24 and the table of FIG. 25 illustrate data obtained through empirical testing of the tips. Subjects applied an uncharacterized amount of downward force with each tip (which was connected to a conventional lancing device), lanced themselves (with a 33 gauge lancet) and then applied downward force for an additional three seconds. The resulting blood volume generated at the lanced site was collected and measured using a 1 µL capillary tube. The results show that the saddle-shaped tip with the oval opening shown in FIGS. 3-5 generated the largest blood volume. The oval opening traps flesh in a radially asymmetric region and hence applies pressure to the skin surrounding the pierced site non-uniformly.

The design of the pressure sleeve necessitates that the user apply at least two pounds of force on the top prior to lancing. Failure to apply this minimum force prevents the lancet from penetrating the fingertip.

Figure 26:
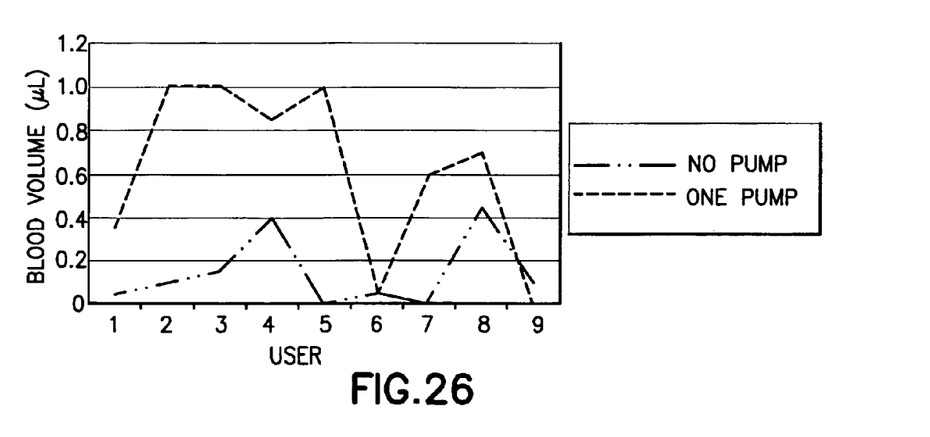
FIG. 26 is a chart comparing pressure application exclusively before lancing or before and after lancing using the pressure sleeve assembly and the saddle-shaped tip having an oval cross section.

An empirical study was undertaken to determine whether the application of pressure prior to lancing alone produced a blood volume commensurate or greater than the application of pressure both before and after lancing. As shown in FIG. 26, the application of pressure both before and after lancing produced a greater volume of blood than is achieved through pressure applied exclusively prior to lancing. The application of pressure after lancing consisted of one pump of the pressure sleeve in which the spring was fully compressed. This means that the secondary pressure application was at least two pounds in value. However, the average value of force applied by each user that exceeded two pounds of force (8.9 newtons) was not characterized. These results clearly illustrate that the application of pressure both before and after lancing facilitates the volume of blood generated.

Other exemplary embodiments of the tip are shown in FIGS. 6-14. Among the various parameters that are changed in the other exemplary embodiments of the tips include the major and minor saddle angles. The surface area, the area of the tip that contacts the fingertip, and the inner and outer diameter of the tip is kept constant in each of the other exemplary embodiments. The variations in saddle angles account for differences in human fingertips. Examples of dimensions of exemplary embodiments of various tips are shown in the table of FIG. 15.

In addition to varying the major and minor saddle angles, other parameters of the tip may be changed, such as the surface area, shape and uniformity of the mating surface. Additionally, the materials used in the tip do not need to be uniform. A tip made from materials of variable compliance may facilitate blood extraction from a lanced site.

Compression springs of augmented or diminished spring rates (stiffness) may be used in the pressure sleeve assembly. A compression spring of a specific value determines the minimum force a user must apply both before and after lancing, but the compression spring does not limit the maximum force that may be applied to the skin.

Figure 27:
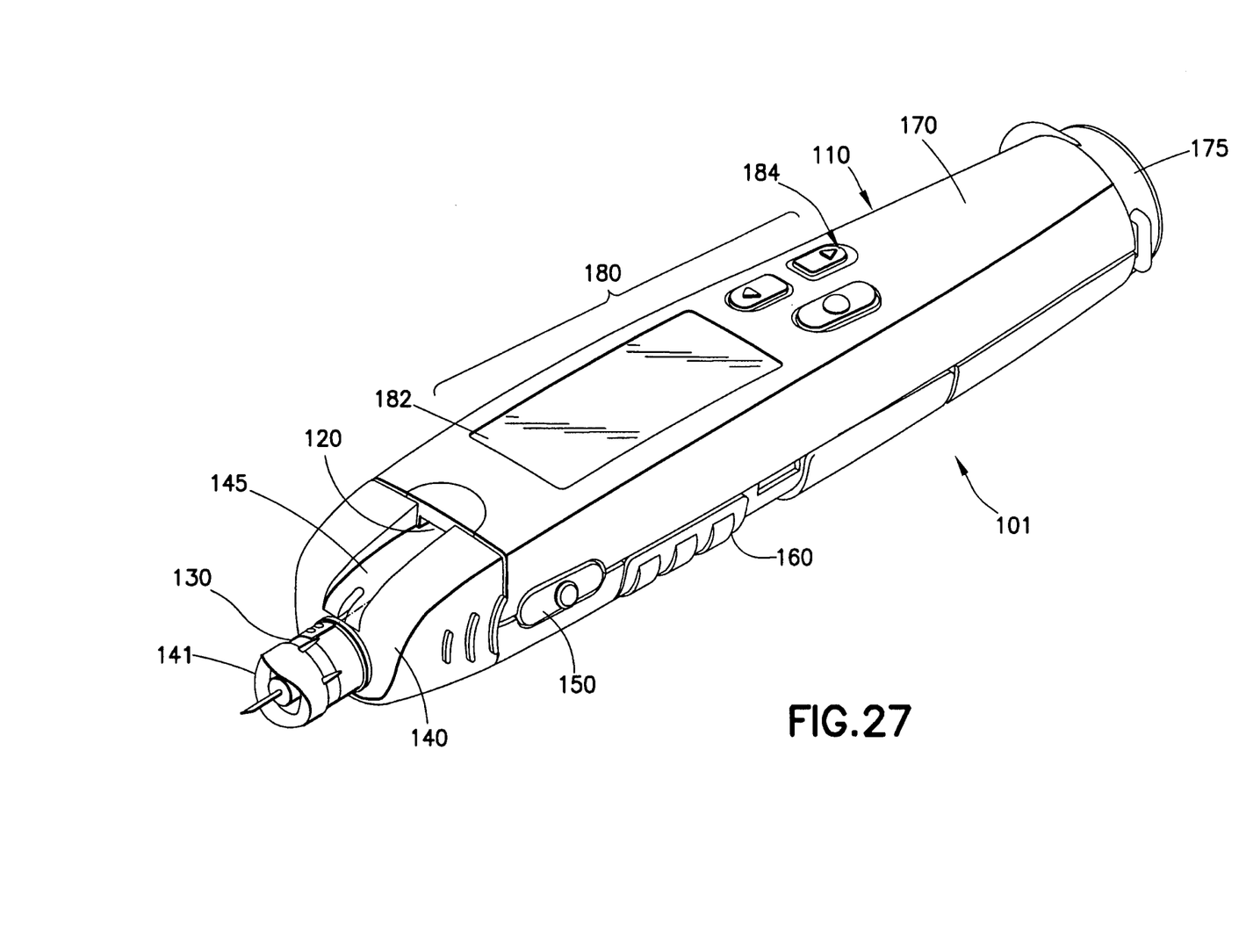
FIG. 27 is a perspective view of a blood glucose meter including a tip having a substantially saddle-shaped distal surface in accordance with another exemplary embodiment of the present invention.

In another exemplary embodiment of the present invention, a blood glucose meter 101 has a saddle-shaped tip 141, as shown in FIG. 27. A detailed description of the blood glucose meter 101 (with a different tip) is provided in commonly-owned U.S. patent application Ser. No. 11/106,728, which was published on Oct. 27, 2005 as U.S. Patent Application Publication No. 2005/0240119, the entirety of which is hereby incorporated by reference. The blood glucose meter 101 includes a device body 110 configured for convenient one-handed use, a test strip port 120 and a lancet device 130 that are disposed at the same end of the device body 110, thereby allowing a drop of blood extracted by the lancet device 130 to be immediately deposited on the test strip (shown in phantom lines) in the test strip port 20. A detachable cover 40 allows lancet replacement and also provides a generous lead-in area 145 to facilitate convenient test strip loading into the test strip port 120. A trigger button 150 on the side of the device body 110 allows comfortable positioning during lancing. The trigger button 150 is mechanically engaged with the lancet mechanism of the lancet device 130 through the device body 110 to activate the lancet as known to those skilled in the art when a force is exerted on the trigger button 150, such as when pressed by a user An arming slide 160 on the sides and bottom of the enclosure of the device body 110 arms the lancing mechanism of the lancet device 130 when moved toward the back of the device, wherein the location of the arming slide 160 keeps the outer size of device body 110 as small as possible. An enclosure 170 houses a test strip vial 175 containing multiple test strips and allows one-handed vial opening. The device body 110 further includes a blood glucose meter 180 for processing the test strip, and a data connector (not shown) located on the bottom of enclosure 170 for data exchanges with an electronic pen-type injector or other device. The blood glucose meter 180 may further include a display window 182 and a plurality of meter operation buttons or controls 184. The enclosure 170 may further include a window (not shown) that allows reading of a test strip lot number on a test strip vial 175 label therein without removing the strip vial from the device body 110. By combining these multiple components into a single device body 110, the device requires fewer steps for testing, and makes device use easier, even in confined or less than ideal locations to test one's blood glucose levels. The saddle-shaped tip 141 is not limited to use with such a blood glucose meter 101 and may be incorporated into any suitable blood glucose meter, such as that described in commonly-owned U.S. Pat. No. 7,192,405 to DeNuzzio et al., the entirety of which is hereby incorporated by reference.

Figure 28:
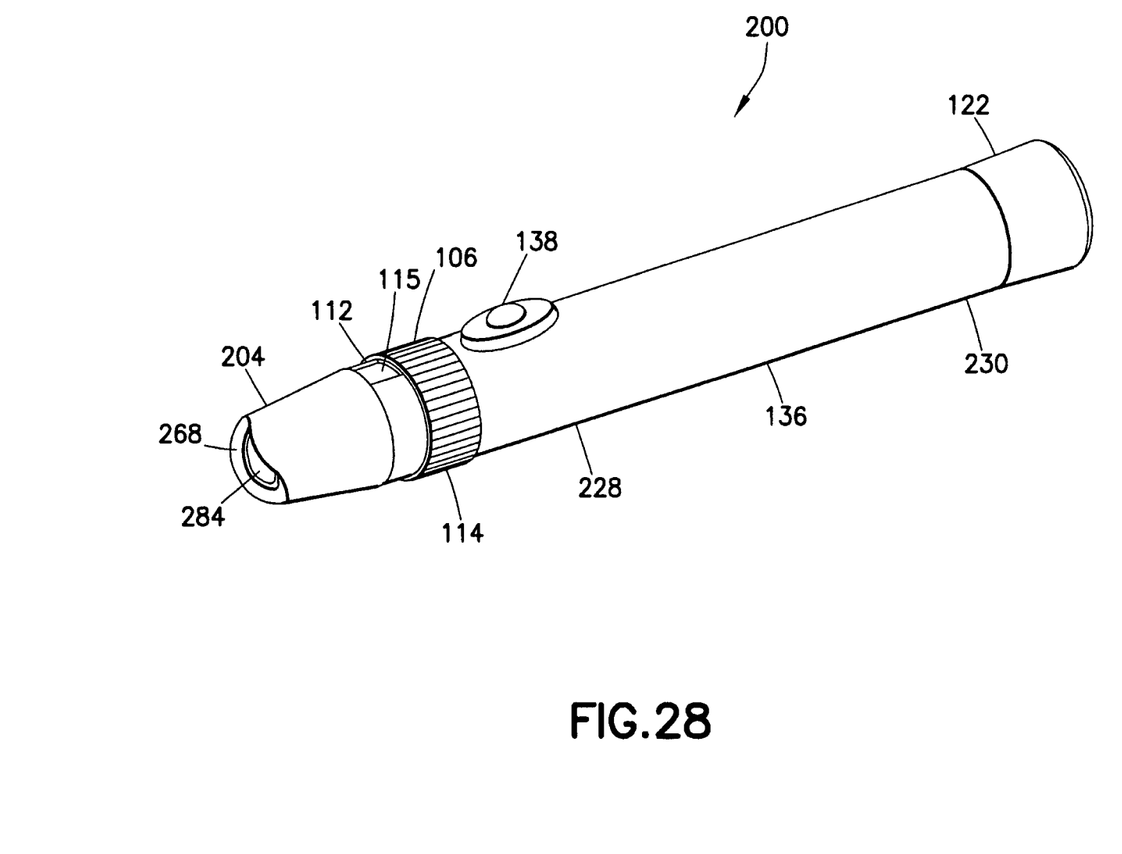
FIG. 28 is a perspective view of a lancing device including a tip having a substantially saddle-shaped distal surface in accordance with another exemplary embodiment of the present invention.

In another exemplary embodiment of the present invention, a lancing device 200, as shown in FIG. 28, includes a tip 204 having a distal surface 268 that is substantially saddle-shaped. An opening 284 in the tip 204 allows a lancet to pass therethrough upon activation of the trigger mechanism by pushing the release member 138. The assembly and operation of the lancing device 200 is substantially similar (except for the tip 204) to that of the lancing device 100 described above with reference to FIG. 1 and to that described in commonly-owned U.S. Pat. No. 6,558,402, which issued on May 6, 2003 and is hereby incorporated by reference in its entirety.

The foregoing embodiments and advantages are merely exemplary and are not to be construed as limiting the scope of the present invention. Various modifications, alternatives and variations will be apparent to those of ordinary skill in the art, and are intended to fall within the scope of the invention as defined in the appended claims and their equivalents.

The invention claimed is:

1. A tip for use with a lancing device, comprising:
a base having an outer perimeter;
a wall extending upwardly from said base and forming a substantially saddle-shaped distal surface for interfacing with a patient's skin, said distal surface has a minor saddle angle between approximately 15 and 20 degrees, inclusive and a major saddle angle between approximately 45 and 60 degrees, inclusive;
an opening extending entirely through said tip, and
a lancet positioned within said opening for lancing the patient's skin.

2. The saddle-shaped tip according to claim 1, wherein said opening is substantially circular.

3. The saddle-shaped tip according to claim 1, wherein said opening is substantially oval.

4. The saddle-shaped tip according to claim 1, wherein said outer perimeter is substantially circular.

5. The saddle-shaped tip according to claim 1, wherein said outer perimeter is substantially oval.

6. A lancing device, comprising:
a tip having a substantially saddle-shaped distal surface for interfacing with a patient's skin, said distal surface having a minor saddle angle between approximately 15 and 20 degrees inclusive, and a major saddle angle between approximately 45 and 60 degrees inclusive; and
a pressure sleeve assembly movably receiving said tip, said pressure sleeve assembly including
a housing;
a pressure sleeve movable between first and second positions;
a spring connected between said housing and said pressure sleeve; and
a lancet rigidly fixed to said housing, said lancet being covered when said pressure sleeve is in said first position and said lancet being exposed through said substantially saddle-shaped distal surface of said tip when said pressure sleeve is in said second position.

7. The lancing device according to claim 6, wherein said tip is connected to said pressure sleeve such that movement of said tip moves said pressure sleeve.

8. The lancing device according to claim 6, wherein said lancet is removably connected to said housing.

9. The lancing device according to claim 6, wherein said spring returns said pressure sleeve to said first position.

10. The lancing device according to claim 6, wherein an oval opening is formed in said tip through which said lancet passes.

11. The lancing device according to claim 6, wherein a circular opening is formed in said tip through which said lancet passes.

12. The lancing device according to claim 6, wherein said lancing device is received by a glucose monitoring device.

13. The lancing device according to claim 6, wherein said distal surface has a circular cross section.

14. The lancing device according to claim 6, wherein said distal surface has an oval cross section.

15. The lancing device according to claim 6, wherein said housing a substantially planar surface opposite said tip for providing stability to said lancing device when applying pressure to said tip.

16. A method of drawing blood, comprising the steps of interfacing a distal surface of a tip of a lancing device with a patient's skin at a lancing site, the distal surface of the tip being substantially saddle-shaped said distal surface having a minor saddle angle between approximately 15 and 20 degrees inclusive, and a major saddle angle between approximately 45 and 60 degrees inclusive; and passing a needle through the saddle-shaped distal surface of the tip to lance the patient's skin at the lancing site.

17. A method of drawing blood according to claim 16, further comprising applying pressure to the tip to pass the needle through the saddle-shaped distal surface of the tip to lance the patient's skin at the lancing site.

18. A method of drawing blood according to claim 16, further comprising activating a trigger mechanism to pass the needle through the saddle-shaped distal surface of the tip to lance the patient's skin at the lancing site.

* * * * *